(12) United States Patent
Farnes et al.

(10) Patent No.: US 9,192,571 B2
(45) Date of Patent: *Nov. 24, 2015

(54) KETOROLAC TROMETHAMINE COMPOSITIONS FOR TREATING OR PREVENTING OCULAR PAIN

(75) Inventors: Eldon Q. Farnes, Laguna Beach, CA (US); Mayssa Attar, Placentia, CA (US); Rhett M. Schiffman, Laguna Beach, CA (US); Chin-Ming Chang, Tustin, CA (US); Richard S. Graham, Irvine, CA (US); Devin F. Welty, Foothill Ranch, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/552,057

(22) Filed: Sep. 1, 2009

(65) Prior Publication Data

US 2010/0087503 A1 Apr. 8, 2010

Related U.S. Application Data

(63) Continuation-in-part of application No. 12/396,131, filed on Mar. 2, 2009, now Pat. No. 7,842,714.

(60) Provisional application No. 61/067,925, filed on Mar. 3, 2008, provisional application No. 61/096,096, filed on Sep. 11, 2008, provisional application No. 61/111,919, filed on Nov. 6, 2008.

(30) Foreign Application Priority Data

Jul. 23, 2009 (AU) ................................ 2009202969

(51) Int. Cl.
| | |
|---|---|
| A61K 31/407 | (2006.01) |
| A61P 27/02 | (2006.01) |
| A61K 9/00 | (2006.01) |
| A61K 9/08 | (2006.01) |
| A61K 31/14 | (2006.01) |
| A61K 47/02 | (2006.01) |
| A61K 47/10 | (2006.01) |
| A61K 47/12 | (2006.01) |
| A61K 47/18 | (2006.01) |
| A61K 47/38 | (2006.01) |

(52) U.S. Cl.
CPC .............. *A61K 9/0048* (2013.01); *A61K 9/08* (2013.01); *A61K 31/14* (2013.01); *A61K 31/407* (2013.01); *A61K 47/02* (2013.01); *A61K 47/10* (2013.01); *A61K 47/12* (2013.01); *A61K 47/186* (2013.01); *A61K 47/38* (2013.01)

(58) Field of Classification Search
None
See application file for complete search history.

(56) References Cited

U.S. PATENT DOCUMENTS

| | | |
|---|---|---|
| 3,278,447 A | 10/1966 | McNicholas |
| 3,890,319 A | 6/1975 | Danielewicz |
| 4,021,416 A | 5/1977 | Locatell, Jr. |
| 4,089,969 A | 5/1978 | Muchowski |
| 4,382,892 A | 5/1983 | Hayakawa |
| 4,407,792 A | 10/1983 | Schoenwald |
| 4,454,151 A | 6/1984 | Waterbury |
| 4,474,787 A | 10/1984 | Cairns |
| 4,522,829 A | 6/1985 | Harting et al. |
| 4,861,514 A | 8/1989 | Hutchings |
| 5,017,229 A | 5/1991 | Burns |
| 5,021,416 A | 6/1991 | Gluchowski |
| 5,045,121 A | 9/1991 | Hoffman |
| 5,089,509 A | 2/1992 | Chandraradna |
| 5,106,615 A | 4/1992 | Dikstein |
| 5,110,493 A | 5/1992 | Cherng-Chyi et al. |
| 5,212,162 A | 5/1993 | Missel |
| 5,215,991 A | 6/1993 | Burke |
| 5,281,591 A | 1/1994 | Burke |
| 5,382,591 A | 1/1995 | Barberich |
| 5,414,011 A | 5/1995 | Fu et al. |
| 5,459,133 A | 10/1995 | Neuffeld |
| 5,460,834 A | 10/1995 | Bhagat |
| 5,527,893 A | 6/1996 | Burns |
| 5,558,876 A | 9/1996 | Desai |
| 5,603,929 A | 2/1997 | Desai |
| 5,648,074 A | 7/1997 | Park |
| 5,658,948 A | 8/1997 | Lucero |
| 5,688,819 A | 11/1997 | Woodward |
| 5,703,077 A | 12/1997 | Burke |

(Continued)

FOREIGN PATENT DOCUMENTS

| | | |
|---|---|---|
| AU | 2009202969 | 11/2009 |
| EP | 0306984 | 3/1989 |

(Continued)

OTHER PUBLICATIONS

Solomon et al (J Cataract Refract Surg, vol. 30, pp. 1653-1660; 2004).*
South African Electronic Package Inserts (Retrieved on Feb. 3, 2012 from the Internet: <URL: http://www.home.intekom.com/pharm/allergan/refre-tr.html, published Nov. 2004).*
Allergan "Refresh Lubricant Eyedrops" retrieved on Apr. 3, 2003 from: www.drugstore.com/qxp72838_333181_sespider/allergan/refresh_liquigel_lubricant_eye_drops.htm.
Aqualon® CMC, Physical and Chemical Properties, Hercules incorporated, printed from http://www.herc.com/aqualon/product_data/brochures/250_10.pdf on Jul. 3, 2008, 1999, 30 pages.
Fodor et al., Mechanism of Tetracaine Block of Cyclic Nucleotide-gated Channels, 1997, J. Gen. Physiol., Abstract printed from http://www.jpg.org/cgi/content/abstract/109/1/3 on Jul. 4, 2008, vol. 109, No. 1, 3-14—Abstract only.

(Continued)

*Primary Examiner* — Jeffrey S. Lundgren
*Assistant Examiner* — Michael Schmitt
(74) *Attorney, Agent, or Firm* — Lorenz Siddiqi

(57) ABSTRACT

The present invention provides an aqueous ophthalmic solution with an effective amount of ketorolac and carboxymethyl cellulose in an aqueous solution which provides increased visual acuity and wherein the concentration of carboxymethyl cellulose is selected to provide an increased absorption of ketorolac in the eye of a patient that is at least 130% greater than the absorption of a comparative aqueous ketorolac ophthalmic solution having the same concentration of ketorolac.

26 Claims, 4 Drawing Sheets

(56) References Cited

U.S. PATENT DOCUMENTS

| | | | |
|---|---|---|---|
| 5,721,275 | A | 2/1998 | Bazzano |
| 5,773,440 | A | 6/1998 | Burke |
| 5,807,541 | A * | 9/1998 | Aberg et al. .................... 424/52 |
| 5,811,446 | A | 9/1998 | Thomas |
| 5,858,346 | A | 1/1999 | Vehige |
| 5,888,493 | A | 3/1999 | Sawaya |
| 5,922,773 | A | 7/1999 | Lipton |
| 6,056,950 | A | 5/2000 | Saettone |
| 6,255,299 | B1 | 7/2001 | Deleuran |
| 6,459,133 | B1 | 10/2002 | Brown et al. |
| 6,627,210 | B2 | 9/2003 | Olejnik |
| 7,045,121 | B2 | 5/2006 | Chang et al. |
| 7,141,607 | B1 | 11/2006 | Si |
| 7,491,383 | B2 | 2/2009 | Woodward |
| RE41,134 | E | 2/2010 | Bazzano |
| 7,842,714 | B2 | 11/2010 | Farnes |
| 8,629,140 | B2 | 1/2014 | Chen et al. |
| 2002/0103255 | A1 | 8/2002 | Hellberg |
| 2002/0198209 | A1 | 12/2002 | Woodward |
| 2002/0198210 | A1 | 12/2002 | Woodward |
| 2003/0069286 | A1 | 4/2003 | Chen |
| 2004/0224010 | A1 | 11/2004 | Hofland |
| 2004/0248962 | A1 | 12/2004 | Muller |
| 2005/0031697 | A1 | 2/2005 | Vehige |
| 2007/0077346 | A1 | 4/2007 | Ellingsen et al. |
| 2007/0254841 | A1 * | 11/2007 | Ousler et al. .................... 514/12 |
| 2007/0287741 | A1 | 12/2007 | Herzberg et al. |
| 2007/0299124 | A1 | 12/2007 | Ousler |
| 2008/0039398 | A1 | 2/2008 | Ousler, III et al. |
| 2008/0070988 | A1 | 3/2008 | Woodward |
| 2008/0275118 | A1 | 11/2008 | Shaw |
| 2009/0010850 | A1 | 1/2009 | Ousler, III et al. |
| 2009/0270392 | A1 | 10/2009 | Old |

FOREIGN PATENT DOCUMENTS

| | | |
|---|---|---|
| EP | 0390071 | 10/1990 |
| EP | 0524587 | 1/1993 |
| EP | 0590786 | 6/1993 |
| EP | 0705878 | 4/1996 |
| GB | 2007091 | 5/1979 |
| RU | 2175561 C2 | 11/2001 |
| WO | WO 92-02515 | 2/1992 |
| WO | WO 92-20349 | 11/1992 |
| WO | WO 93-17664 | 9/1993 |
| WO | WO 00-54762 | 9/2000 |
| WO | WO 01-01959 | 1/2001 |
| WO | WO 02-05853 | 1/2002 |
| WO | WO 03-051332 | 6/2003 |
| WO | WO 2004-112750 | 12/2004 |
| WO | 2005-014046 | 2/2005 |
| WO | WO2005/101982 | 11/2005 |
| WO | WO2006/071601 | 7/2006 |
| WO | WO2008153746 A1 | 12/2008 |
| WO | WO2009/111418 | 9/2009 |

OTHER PUBLICATIONS

LaMotte et al.: The Effect of Artificial Tears With Different CMC Formulations on Contrast Sensitivity. ARVO Annual Meeting Abstract Search and Program Planner, vol. 2002, 2002 p. Abstract No. 3151.

MayoClinic.com, Dry Eyes, Printed from http://www.mayoclinic.com/health/dry-eyes/DS00463/METHOD=print&DSECTION=all on Jul. 1, 2010, 14 pages.

MedlinePlus, U.s. National Library of Medicine and National Institues of Health, Dry Eye Syndrome, Printed from http://www.nlm.nih.gov/medlineplus/ency/article/000426.htm on Jul. 1, 2010, 2 pages.

Simmons P.A.: Refresh Liquigel ™: A New Approach to the Treatment of Persistent Dry Eye, Practical Optometry 2002 Canada, vol. 13, No. 2, 2002, pp. 68-71.

UIC Department of Ophthalmology and Visual Sciences, Dry Eyes, Printed from http://www.uic.edu/com/eye/learningaboutvision/eyefacts/dryeyes.shtml on Jul. 1, 2010, 6 pages.

www.rxlist.com, Alcaine-Clinical Pharmacology, http://www.rxlist.com/cgi/generic/propara_cp.htm, printed Jul. 4, 2008, 2 pages.

Guidera et al, Ophthalmology, 2001, 108 (5), pp. 936-944.

Solomon et al, J Cataract Refract Surg, 2001, 27 (8), pp. 1232-1237.

Teal et al, J Cataract Refract Surg, 1995, 21(5) , pp. 516-518.

Jaanus et al, Antiinflammatory Drugs. Clinical Ocular Pharmacology, Bartlet, J.D. and Jaanus, S.D., Ed., Boston: Heineman, 2001, pp. 265-298.

Waterbury, et al., *Efficacy of Low Concentrations of Ketorolac Tromethamine in Animal Models of Ocular Inflammation*, 2004, vol. 20, No. 4, pp. 345-352.

Waterbury, et al., *Comparison of Ketorolac Tromethamine, Dlclofenac Sodium, and Loteprednol Etabonate in an Animal Model of Ocular Inflammation*, 2006, vol. 32, No. 3, pp. 155-159.

Price F, Tonen E, VanDenburgh A, Cheetham JK, Schiffman R. Safety and efficacy of reformulated ketorolac tromethamine 0.4% ophthalmic solution in post-photorefractive keratectomy patients. Association for Research and Vision in Ophthalmology 2003: Poster 2611. Presented May 6, 2003 at 8:30:00 AM.

Sandoval et al.; "Evaluation of 0.4% Ketorolac Tromethamine Ophthalmic Solution Versus 0.5% Ketorolac Tromethamine Ophthalmic Solution After Phacoemulsification and Intraocular Lens Implantation" Journal of Ocular Pharmacology and Therapeutics vol. 22, No. 4, 2006; pp. 251-257.

Whittpenn "Acular LS: Reduced Discomfort without Loss of Efficiency" Ophthalmology Management, May 2005.

Ahuja, M et al. The AAPS Journal. 2008. vol. 10(2): 229-241.

U.S. Appl. No. 10/911,966, filed Aug. 5, 2004, Joseph G. Vehige.

U.S. Appl. No. 60/478,713, filed Jun. 13, 2003, Chowan.

Allergan "Optive Lubricant Eye Drops" retrieved from: https://www.wegmans.com/webapp/wcs/ stores/servlet/ProductDisplay?langId=-1&storeId=10052&productId=386017& catalogId=10002&krypto=QJrbAudPdOvzXUG Byeatog%3D%3D &ddkey=http:ProductDisplay.

Rossi, S.; et al.: Drug Release and Washability of Mucoadhesive Gels Based on Sodium Carboxymethylcellulose and Polyacrylic Acid, Pharm. Dev. Tech., 4(1), 55-63 (1999).

Abrams, Thomas (Food and Drug Administration, Rockville, MD). "Warning Letter" to Pyott, David (Allergan, Inc., Irvine). 7 pages, May 25, 2007.

Acular® Product Label, 5 pages, Retrieval Date: Jan. 6, 2012, http://www.drugs.com/pro/acular.html?printable=1.

Acular LS® Prescription Information, 4 pages, Retrieval Date: Jan. 6, 2012, http://www.allergan.com/assets/pdf/acular_ls_pi.pdf.

Acular PF, 5 pages, Retrieval Date: Jan. 6, 2012, http://www.drugs.com/pro/acular-pf.html?printable=1.

Antimicrobial Effectiveness Testing, 26 U.S. Pharmacopeia 2002 (2003),p. 2002-2004.

Assouline, Michael et al., "A Prospective Randomized Trial of Topical Soluble 0.1% Indomethacin Versus 0.1% Dislofenac Versus Placebo for the Control of Pain Following Excimer Laser Photorefractive Keratectomy", 29(5), Ophthalmic Surgery Laser 365 (1998),p. 365-374.

Banker, Gilbert & Rhodes, Christopher, 121 Modern Pharmaceutics 450, 676 (2002),p. 450.

Bapatla, Krishna M. & Hecht, Gerald, "Ophthalmic Ointments and Suspensions", in Pharmaceutical Dosage Forms: Disperse Systems 461 (Herbert A. Lieberman et al. eds., 1989),p. 461-494.

Boylan, J.C., "Liquids", in The Theory and Practice of Industrial Pharmacy 457 (Leon Lachman et al. eds., $3^{rd}$ ed. 1986),p. 457-478.

Burgalassi, Susi et al., "Cytotoxicity of Potential Ocular Permeation Enhancers Evaluated on Rabbit and Human Corneal Epithelial Cell Lines", 122(1) Toxicol. Lett. 1 (2001),p. 1-8.

Carter, S.J., Ophthalmic Products, Cooper & Gunn's Dispensing for Pharmaceutical Students, $12^{th}$ Edition, pp. 634-662 (2000).

Chiambaretta, F. et al., "Ocular Tolerance of a New Formulation of Nonpreserved Diclofenac", 27 (7), J. Fr. Ophthalmol. 739 (2004) (English Abstract).

Fiedler, M.A., "Clinical Implications of Ketorolac for Postoperative Analgesia", 12 (6) J. Perianesthesia Nursing at Table IV (1997),p. 426-433.

(56) References Cited

OTHER PUBLICATIONS

Flach, Allan, "Topically Applied Nonsteroidal Anti-inflammatory Drugs and Corneal Problems: An Interim Review and Comment", 107(7), Ophthalmology 1224 (2000),p. 1224-1226.
Furrer, Pascal et al., "Ocular Tolerance of Absorption Enhancers in Ophthalmic Preparations", 4(1), AAPS Pharm. Sci. 1-5 (2002).
Furrer, Pascal et al., "Ocular Tolerance of Preservatives and Alternatives", 53, Eur. J. Pharm. & Biopharm., 263-280 (2002).
Gaynes, Bruce I. & Fiscella, Richard, "Topical Nonsteroidal Anti-Inflammatory Drugs for Ophthalmic Use: A Safety Review", 25(4), Drug Safety, 233-250 (2002).
Hecht, Gerald, "Ophthalmic Preparations", in Remington: The Science & Practice of Pharmacy 821 (Alfonso R. Gennaro ed., $20^{th}$ ed. 2000),p. 821-835.
Kronemyer, Bob, "Acular Reformulated to Reduce Ocular Pain, Burning, Stinging", Ocul. Surg. News, Sep. 15;21(18),48, 2003.
Madhu, Cherukury et al., "Effect of Benzalkonium Chloride/EDTA on the Ocular Bioavailability of Ketorolac Tromethamine Following Ocular Instillation to Normal and Deepithelialized Corneas of Rabbits", 85(4) J. Pharm. Sci. 415 (1996),p. 415-418.
Malcolm Rowland & Thomas N. Tozer, Clinical Pharmacokinetics: Concepts and Applications 61 ($3^{rd}$ ed. 1995),p. 61.
Manjusha Malhotra & D.K. Majumdar, "Effect of Preservative, Antioxidant and Viscolizing Agents on In Vitro Transcorneal Permeation of Ketorolac Tromethamine", 40 Indian J. Exp. Biol. 555 (2002),p. 555-559.
R.J. Marsh & D. M. Maurice, "The Influence of Non-Ionic Detergents and Other Surfactants on Human Corneal Permeability", 11 Exp. Eye Res. 43 (1971),p. 43-48.
Maurer, James K. et al., "Ocular Irritation: Pathological Changes Occurring in the Rat with Surfactants of Unknown Irritancy", 26(2) Toxicologic Pathol. 226-233 (1998).
Maurer, James K. et al., "Ocular Irritation: Microscopic Changes Occurring Over Time in the Rat with Surfactants of Known Irritancy", 26(2) Toxicol Pathol. 217-225 (1998).
Missotten, Luc et al., "Topical 0.1% Indomethacin Solution Versus Topical 0.1% Dexamethasone Solution in the Prevention of Inflammation After Cataract Surgery", 215(1) Ophthalmologica 43, 43 (2001).
Ophthalmic Nonsteroidal Anti-Inflammatory Drugs (NSAIDs) Review, Provider Synergies, L.L.C., 8 pages, Sep. 2008.
Ophthalmic Ointments, 26 U.S. Pharmacopeia 2183 (2003),p. 2183-2184.
The Cosmetic Ingredient Review Expert Panel, Safety Assessment of Salicyclic Acid, Butyloctyl Salicylate, Calcium Salicylate, C12-15 Alky Salicylate, Capryloyl Salicylic Acid, Hexyldodecyl Salicylate, Isocetyl Salicylate, Isodecyl Salicylate, Magnesium Salicylate, MEA—Salicylate, Ethylhexyl Salicylate, Potassium Salicylate, Methyl Salicylate, Myristy Salicylate, Sodium Salicylate, TEA—Salicylate, and Tridecyl Salicylate, 22 (Suppl. 3) Int'l J. Toxicology 1 (2003),p. 1-108.
Rooks II, Wendell H. et al., "The Analgesic and Anti-Inflammatory profile of Ketorolac and Its Tromethamine Salt", XI (8) Drugs Exptl. Clin. Res. 479 (1985),p. 479-492.
Rooks II, Wendell H., "The Pharmacologic Activity of Ketorolac Tromethamine", 10 (6 Supp) Pharmacotherapy 30S (1990),p. 30S-32S.
Ruggiero, Ronald J., "Prescription Contraceptives: Countering the Risks", NS25 (9) Am. Pharm. 32 (1985),p. 32-37.
Sasaki, Hitoshi et al., "Ophthalmic Preservatives as Absorption Promoters for Ocular Drug Delivery", 47 J. Pharm. Pharmacol. 703 (1995),p. 703-707.
Sheppard, John, "Using NSAIDs to Full Potential: Expert Guidance on Maximizing Utility", Safety and Efficacy, Ophthalmology MGMT. 1,2 (Nov. 2001).
P. Heinrich Stahl & Camille G. Wermuth, Handbook of Pharmaceutical Salts: Properties, Selection, and Use 325 (2002),p. 324-325.
Tutton, Miles K. et al., "Efficacy and Safety of Topical Diclofenac in Reducing Ocular Pain After Excimer Photorefractive Keratectomy", 22(5) J. Cataract Refractive Surgery 536, 536 (1996),p. 536-541.

Malhotra, Manjusha et al., In Vitro Transcorneal Permeation of Ketorolac From Oil Based Ocular Drops and Ophthalmic Ointment, Indian Journal of Experimental Biology, vol. 35, Dec. 1997, p. 1324-1330.
Malhotra, Manjusha et al., In Vivo Ocular Availability of Ketorolac Following Ocular Instillations of Aqueous, Oil, and Ointment Formulations to Normal Corneas of Rabbits: A Technical Note, AAPS PharmSciTech, vol. 6 (3), 2005, p. E523-E526.
Koay, Peter, Reply—The Emerging Roles of Topical Non-Steroidal Anti-Inflammatory Agents in Ophthalmology, Brit. J. Ophthalmology, vol. 80, 1996, p. 480.
Allergan "Optive Lubricant Eye Drops" retrieved on Jan. 5, 2011 from:https ://www.wegmans.com/webapp/wcs/stores/servlet/ProductDisplay?langId=1&storeId=10052&productId=386017&catalogId=10002&krypto=QJrbAudPdOvzXUGByeatog%3D%3D&ddkey=http:ProductDisplay.
Flach, AJ et al, The Effect of Ketorolac Tromethamine in Reducing Postoperative Inflammation: Double-Mask Parallel Comparison with Dexamethasone, Ann Ophthalmol, 1989, vol. 21(11), p. 407-411 (Abstract).
Islam, MR, Citrate Can Effectively Replace Bicarbonate in Oral Rehydration Salts for Cholera and Infantile Diarrhoea, Bull World Health Organ., 1986, vol. 64(1), p. 145-150 (Abstract).
Rossi, S. et al., Drug Release and Washability of Mucoadhesive Gels Based on Sodium Carboxymethylcellulose and Polyacrylic Acid, Pharmaceutical Development and Technology, 1999, vol. 4(1), p. 55-63.
Eric D. Donnenfeld et al, Jul. 1, 2007, Double-Masked Study of the Effects of Nepafenac 0.1% and Ketorolac 0.4% on Corneal Epithelial Wound Healing and Pain After Photorefractive Keratechtomy, Advances in Therapy, 24 (4), 852-862.
Keping Xu, 2011, Ex vivo corneal Epithelial wound healing following exposure to ophthalmic nonsteroidal anti-inflammatory drugs, Clinical Ophthalmology, 5(1), 269-274.
Mao Kusano et al, 2010, Evaluation of Acute Corneal Barrier Change Induced by Topically Applied Preservatives Using Corneal Transepithelial Electric Resistance in Vivo, Cornea, 29 (1), 80-85.
Qian Garrett et al, 2008, Carboxymethyl Cellulose Stimulates Rabbit Corneal Epithelial Wound Healing, Current Eye Research, 33 (7), 567-573, Informa Healthcare.
Seung-Heon Cha et al, 2004, Corneal Epithelial Cellular Dysfunction From Benzalkonium Chloride (BAC) in vitro, Clinical and Experimental Opthalmology, 32(2), 180-184.
W. Barry Lee et al, 2006, Corneal Ulceration and Perforation With Ketorolac Tromethamine, Cornea, 25 (10), 1268.
Akron Inc.'s Initial invalidity Contentions, Jul. 20, 2012, 19 Pages.
Rowe, Raymond et al, Sodium Citrate Dihydrate, Handbook of Pharmaceutical Excipients, 2006, 675-677, 5th Edition, Pharmaceutical Press.
Solomon, KD et al, Topical Ketorolac Tromethamine 0.5% Ophthalmic Solution in Ocular Inflammation After Cataract Surgery, Ophthalmology, Feb. 2001, 331-7 (Abstract Only) 2 pages, 108(2).
U.S. Appl. No. 60/478,713, filed Jun. 13, 2003.
Islam, MR, Citrate Can Effectively Replace Bicarbonate in Oral Rehydration Salts for Cholera and Infantile Diarrhoea, Bull World Health Organ., 1986, vol. 64(1), pp. 145-150 (Abstract).
McDonald, M., A Return to PRK, Cataract & Refractive Surgery Today, May 2007, pp. 75-77.
Garrett, Q. et al., Carboxymethylcellulose Binds to Human Corneal Epithelial Cells and Is a Modulator of Corneal Epithelial Wound Healing, Invest. Ophthamol. Vis. Sci. 2007, 48: 1559-1567, 4.
Acuvail (ketorolac tromethamine)—Drug information from MediLexicon, Sep. 17, 2010, retrieved from URL: http://web.archive.org/web/20100917233536/http://www.medilexicon.com/drugs/acuvail.php [retrieved on Nov. 19, 2014].
Refreash TEARSn Lubricating eye drops, Nov. 2004, printed from http://home.intekom.com/pharm/refre-tr.html, 3 pages.
Price, M. et al., Efficacy of topical ketorolac tromethamine 0.4% for control of pain or discomfort associated with cataract surgery, Curr. Med. Res. & Opinion, 2004, 20: 2015-2019, 12.

* cited by examiner

|  | 0.45% Ketorolac | Acular LS® |
|---|---|---|
| Cmax (ng/mL) | 456 | 310 |
| AUC0-t (ng·h/mL) | 2230 | 1467 |
| %Relative Bioavailability | 178 | 100 |

|  | 0.45% Ketorolac | Acular LS® |
|---|---|---|
| Cmax (ng/g) | 429 | 216 |
| AUC0-∞ (ng·h/g) | 5090 | 1860 |
| %Relative Bioavailability | 285 | 100 |

|  | 0.45% Ketorolac BID | Acular LS ® QID |
|---|---|---|
| AUC0-τ (ng·hr/g) | 2910 | 725 |

FIG. 6

| Variable | Ketorolac 0.45% | ACULAR LS 0.40% |
|---|---|---|
| Ocular AEs-Irritation | 10.0% (2/20) | 15.4% (6/39) |
| Symptoms-Burning/stinging ($\geq$ 1 grade increase) | 10.0% (2/20) | 12.8% (5/39) |
| Bulbar hyperemia ($\geq$ trace) | 10.0% (2/20) | 23.1% (9/39) |
| Ocular comfort ($\geq$ comfortable) | 90-100% | 84-100% |

KETOROLAC TROMETHAMINE COMPOSITIONS FOR TREATING OR PREVENTING OCULAR PAIN

RELATED APPLICATION

This application claims the benefit of U.S. patent application Ser. No. 12/396,131 filed on Mar. 2, 2009 pursuant to 35 USC 120 which application claims the benefit of and priority to U.S. provisional application Ser. Nos. 61/067,925 filed Mar. 3, 2008, 61/096,096 filed Sep. 11, 2008, and 61/111,919 filed Nov. 6, 2008, and to Australian Patent Application No. 2009202969 filed on Jul. 23, 2009 pursuant to 35 USC 119, all of which prior applications are incorporated herein by reference in their entireties.

FIELD OF THE INVENTION

This invention relates to pharmaceutical compositions. More particularly, this invention relates to topical ophthalmic solutions comprising 5-benzyl-2,3-dihydro-1H-pyrrolizine-1-carboxylic acid, otherwise known as ketorolac, and the use of ketorolac for treating or preventing ocular pain.

DESCRIPTION OF THE RELATED ART

Topical nonsteroidal anti-inflammatory drugs (NSAIDs) are used to control pain and postoperative inflammation. All drugs are associated with some adverse effects. With the use of NSAIDS in topical ophthalmic treatment of patients, surface toxicity has been a concern, and incidents of keratitis, corneal subepithelial infiltrates, ulceration, and corneal melts have been reported (Guidera et al, *Opthalmology*, 2001, 108 (5), pp. 936-944; Solomon et al, *J Cataract Refract Surg*, 2001, 27 (8), pp. 1232-1237; Teal et al, *J Cataract Refract Surg*, 1995, 21(5), pp. 516-518). Further, patients often report burning or stinging on instillation (Jaanus et al, Antiinflammatory Drugs. Clinical Ocular Pharmacology, Bartlet, J. D. and Jaanus, S. D., Ed., Boston: Heineman, 2001, pp. 265-298). The burning or stinging could be related to the concentration of the active component of the formulation.

Ketorolac tromethamine 0.5% (w/v) ophthalmic solution, available from Allergan, Inc., under the tradename ACULAR®, is a safe and effective NSAID with proven analgesic and anti-inflammatory activity. The most common adverse event associated with the use of the 0.5% ketorolac formulation is ocular irritation, primarily burning and stinging upon instillation. Ketorolac tromethamine 0.4% (w/v) ophthalmic solution, under the tradename ACULAR LS®, has shown improved bioavailability and less stinging on instillation than ACULAR®, but there remains a need for an improved ketorolac tromethamine formulation with greater bioavailability and greater tolerability, minimized ocular surface toxicity, improved patient comfort, increased retention time of the active ingredient and improved wound healing capabilities during use.

It is one object of this invention to provide a ketorolac formulation for instillation in the eye to eliminate or reduce ocular irritation, to improve tolerability, compliance, duration and effect of ketorolac, to allow for dosing from four times daily to twice daily, and to increase the effectiveness of treatment by being free of benzalkonium chloride or other preservatives.

It is another object of the invention to improve bioavailability and increase the ocular absorption of ketorolac yet provide an aqueous solution having an optimized concentration of ketorolac.

It is another object of the invention to extend the effects of ketorolac and allow for a decrease in required daily dosage.

It is another object of the invention to provide reduction of inflammation associated with cataract surgery and reduction of pain associated with cataract surgery in comparison to other ketorolac formulations.

It is another object of the invention to create a ketorolac formulation with improved wound healing capabilities.

Other objects of this invention will become apparent from a reading of the present specification.

SUMMARY OF THE INVENTION

Figures 1, 2:
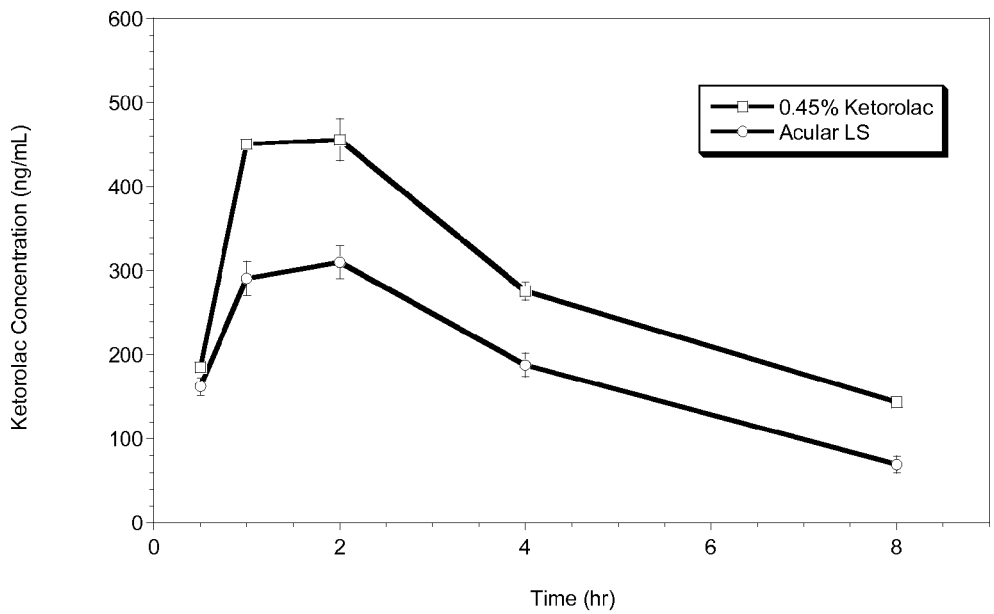
FIG. 1 shows the ocular pharmacokinetics of the results in Example 7 of the increased and prolonged ketorolac exposure in the aqueous humor of the 0.45% w/v ketorolac solution in comparison to ACULAR LS®.
FIG. 2 shows the results of FIG. 1 in table form of Cmax, AUC and percent relative bioavailability of the ocular pharmacokinetics in Example 7 of the aqueous humor relative bioavailability of 0.45% w/v ketorolac solution in comparison to ACULAR LS®.

The present invention provides an aqueous ophthalmic formulation comprising an effective amount of ketorolac but having an optimized concentration of ketorolac in comparison other commercially available ketorolac products. The aqueous ophthalmic solution of the present invention comprises carboxymethyl cellulose, e.g. sodium carboxymethyl cellulose, having a pH within the range of from about 6.8 to 7.4, which is comfortable when topically applied to the eye of a patient, wherein the concentration of carboxymethyl cellulose and, preferably, the pH, is selected to provide an increased absorption of ketorolac in the eye of a patient as compared to a comparative ketorolac solution that differs only in not including the carboxymethyl cellulose. That is, the absorption of ketorolac may be 130% or greater than the absorption of a comparative aqueous ketorolac ophthalmic solution having the same or higher concentration of ketorolac.

More preferably, the aqueous ophthalmic solution of this invention has a pH within the range of from 6.8 to 7.4, particularly 6.8.

More preferably, the aqueous ophthalmic solution of the present invention has a concentration of carboxymethyl cellulose of from about 0.2 to about 2 percent, by weight, even more preferably from about 0.5 to 1.5 percent, by weight, and most preferably about 0.5% w/v.

Even more preferably, the aqueous ophthalmic solution of the present invention comprises a mixture of medium viscosity and high viscosity sodium carboxymethyl cellulose.

More preferably, the aqueous ophthalmic solution of the invention comprises an effective amount of ketorolac of from 0.25 to 0.50 percent, by weight, or about 0.45 percent, by weight.

More preferably, the aqueous ophthalmic solution of the invention has a viscosity of from 5 to 50 cps, preferably from 10 to 30 cps.

It has been surprisingly discovered that optimizing the concentration of ketorolac tromethamine reduces the occurrence of adverse events while maintaining clinical efficacy. Additionally, it has been discovered that the optimized concentration of ketorolac tromethamine in combination with carboxymethyl cellulose offers surprising and clear benefits in terms of formulation in that no preservative, chelating agent, and surfactant are required for formulation. Thus, finding a way to increase the absorption of ketorolac benefits the patient who can use a solution having an optimized concentration of ketorolac and obtain similar results in terms of efficiency as compared to a ketorolac solution having a higher concentration of ketorolac.

Thus, this invention relates to an aqueous topical ophthalmic composition comprising 0.25 to 0.50 percent by weight, more preferably from 0.35% to 0.45% by weight and most preferably about 0.45% ketorolac tromethamine by weight/volume. The present invention also contains from 0.2 to 2 percent by weight, more preferably from 0.5 to 1.5 percent by weight and most preferably about 0.5% w/v percent of medium and high molecular weight sodium carboxymethyl cellulose. Another aspect of this invention relates to a method of treating or preventing ocular pain in a person comprising topically administering to said patient a sterile composition comprising from 0.25 to 0.50 percent, by weight, more particularly from 0.35% to 0.45% by weight, or about 0.45% w/v ketorolac tromethamine in combination with from 0.2 to 2 percent, by weight, preferably from 0.5 to 1.5 percent by weight, and most preferably 0.5% percent by weight/volume, sodium carboxymethyl cellulose and mixtures thereof.

While not intending to limit the scope of this invention in any way, of particular interest in relationship to this invention is the use of aqueous topical ophthalmic compositions of 0.45% (w/v) ketorolac tromethamine for the treatment of ocular pain, especially for the treatment of ocular pain in postoperative photorefractive keratectomy (PRK) surgery patients which improves healing. It is surprising that the lower concentration of ketorolac as compared to the Acular® product, discussed herein, would reduce the incidence of adverse events and enhance comfort while maintaining clinical efficacy. Two drops (0.1 mL) of 0.5% ketorolac tromethamine ophthalmic solution instilled into the eyes of patients 12 hours and 1 hour prior to cataract extraction achieved measurable levels in 8 of 9 patients' eyes (mean ketorolac concentration 95 ng/mL aqueous humor, range 40 to 170 ng/mL). Ocular administration of ketorolac tromethamine reduces prostaglandin $E_2$ ($PGE_2$) levels in aqueous humor. The mean concentration of $PGE_2$ was 80 pg/mL in the aqueous humor of eyes receiving vehicle and 28 pg/mL in the eyes receiving 0.5% ketorolac tromethamine ophthalmic solution.

Ocular administration of 0.45% w/v ketorolac tromethamine ophthalmic solution increases relative bioavailability of ketorolac in the aqueous humor of rabbits to greater than 200% and in the iris-ciliary body to nearly 300%, compared with 0.5% ketorolac tromethamine ophthalmic solution. This enhanced ketorolac bioavailability allows for a reduction in dosing frequency from QID with 0.5% ketorolac tromethamine ophthalmic solution to BID with 0.45% ketorolac solution. Preclinical data indicate systemic ketorolac exposure levels achieved following ocular administration of 0.45% ketorolac solution are comparable to levels achieved with 0.5% ketorolac tromethamine ophthalmic solution.

DETAILED DESCRIPTION OF THE INVENTION

During the reformulation of Allergan's marketed Acular LS® product (0.40% w/v ketorolac), it was surprisingly found that a test formulation containing 0.45% ketorolac tromethamine and sodium carboxymethyl cellulose (NaCMC) exhibited significantly better ocular absorption in rabbits than did the currently marketed product, i.e. Acular LS®.

Since the viscosities of the two test solutions were virtually identical, the mechanism for achieving increased ocular penetration compared to the control formulation cannot be accounted for only by the viscosity of the test solutions. In fact, a comparison of two identical carboxymethyl cellulose-containing solutions which differ only in having viscosity of 11 and 22 cps shows similar absorption of ketorolac into the aqueous humor. While not wishing to be bound by theory, it is believed that there is a functional relationship between the sodium carboxymethyl cellulose and either the ketorolac or some component of the ocular surface that facilitates absorption of ketorolac.

All of the aqueous topical ophthalmic solutions of this invention are contemplated for use in treating or preventing ocular pain. Preferably, all of the solutions of this invention are contemplated for use when said ocular pain is a result of photorefractive keratectomy surgery (PRK).

One important aspect of this invention is that the solutions of the present invention have a concentration of ketorolac tromethamine which is optimized to reduce side effects, while maintaining clinical efficacy in treating ocular pain. As such, the concentration of ketorolac tromethamine in compositions related to this invention is preferably from 0.35% to 0.45% w/v, most preferably the concentration of ketorolac tromethamine in the aqueous topical ophthalmic solution of this invention is 0.45% ketorolac tromethamine, by weight.

Carboxymethyl cellulose (CMC) is a carboxymethyl derivative of cellulose formed by the reaction of cellulose with alkali and chloroacetic acid. As a result of said reaction, carboxymethyl groups are bound to some of the hydroxyl groups of the glucopyranose units that make up the backbone of cellulose. The degree of substitution of carboxymethyl varies from about 0.6 to 0.95 per glucopyranose unit. CMC is used in aqueous solutions usually as the sodium salt to increase viscosity.

Carboxymethyl cellulose is available in various molecular weights. Low molecular weight carboxymethyl cellulose has a Mw of about 90,000 daltons and a 2% solution thereof will have a viscosity of about 1.1 cP at 25° C. Medium weight carboxymethyl cellulose has a Mw of about 250,000 daltons. High molecular weight carboxymethyl cellulose has a Mw of about 700,000 daltons and a 2% solution will have a viscosity of about 12 cP at 25° C.

For the purpose of the present invention, it is desirable to use a mixture of medium and high molecular weight sodium carboxymethyl cellulose. For example, from 25/75 to 75/25 carboxymethyl cellulose, preferably from 30/70 to 70/30 and most preferably about 35/65 medium/high molecular weight sodium carboxymethyl cellulose or most preferably a ratio of 0.325/0.175.

The fact that the concentration of ketorolac tromethamine in compositions related to this invention achieves greater or equal absorption of ketorolac into the aqueous humor of the eye and includes carboxymethyl cellulose, allows the solutions of the present invention to be prepared with no preservative, surfactant and chelating agent. This is a significant advantage over prior art ketorolac formulations as preservatives, surfactants and chelating agents can cause irritation to the eye resulting in less patient compliance and less effectiveness of prior art ketorolac formulations.

The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. Preferably, the ketorolac solution of the present invention is preservative free.

The term surfactant used in this invention has the meaning commonly understood in the art. Surfactants are used to help solubilize the therapeutically active agent or other insoluble components of the composition. Anionic, cationic, amphoteric, zwitterionic, and nonionic surfactants may all be used in this invention. If a surfactant is included in the solutions of this invention, preferably, a nonionic surfactant is used. While not intending to limit the scope of the invention, some examples of useful nonionic surfactants are polysorbates, poloxamers, alcohol ethoxylates, ethylene glycol-propylene glycol block copolymers, fatty acid amides, and alkylphenol ethoxylates, and phospholipids. Most preferably, the surfactant is an octylphenol ethoxylate with an average of 40 ethoxylate groups. This type of surfactant, also known as octoxynol-40 or Igepal CA-897®, can be purchased under the Igepal CA-897® tradename from Rhône-Poulenc. Preferably, the ketorolac solution of the present invention is surfactant free.

The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts like edetate disodium, edetate calcium disodium, edetate sodium, edetate trisodium, and edetate dipotassium. Preferably, the ketorolac solution of the present invention is chelator free.

In addition to surfactants, preservatives, and chelating agents, tonicity agents and other excipients are often used in ophthalmic compositions. Tonicity agents are often used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. Preferably, the tonicity agent is sodium chloride.

One preferred embodiment of this invention relates to an aqueous topical ophthalmic composition comprising 0.4% ketorolac tromethamine, from 0.2 to 2.0%, by weight, sodium carboxymethyl cellulose.

The most preferred embodiment of this invention relates to an aqueous topical ophthalmic composition consisting of 0.45% (w/v) of ketorolac tromethamine, 0.5% w/v of carboxymethyl cellulose sodium, e.g. a mixture of medium and high viscosity sodium carboxymethyl cellulose, sodium chloride, sodium citrate dehydrate, sodium hydroxide, hydrochloric acid and purified water.

Example 1

Unless otherwise specified, all steps in this procedure were carried out at room temperature. The following procedure was followed in accordance with the amounts listed in Table 1 below. Purified water was charged into the main batch vessel. Mixing was initiated to produce a vortex sufficient to disperse and/or dissolve all product ingredients without excessive aeration or foam formation. The following components were added directly into the vortex in order, allowing each to dissolve before adding the next: sodium chloride, calcium chloride, dihydrate magnesium chloride, hexahydrate, boric acid, sodium borate, sodium carboxymethyl cellulose as a an percent aqueous solution comprising including a mixture of 65% medium molecular weight and 35% high molecular weight carboxymethyl cellulose. The solution was mixed for no longer than 15 minutes. A specified amount of 1N sodium hydroxide, was then added. The pH was checked and, if needed, was adjusted to 7.3 with 1N sodium hydroxide or 1N hydrochloric acid. Ketorolac tromethamine was then added based on "as is" assay and mixed until completely dissolved based on visual inspection. When dissolved, the solution pH was again checked and if needed adjusted to pH 7.3-7.5 (final target pH is 7.4) with 1N sodium hydroxide or 1N hydrochloric acid. Purified water was then added to bring the bulk solution to final volume and allowed to mix for at least 15 minutes to ensure uniformity. The solution was then sterile filtered for use.

TABLE 1

| 0.4% Ketorolac Tromethamine Ophthalmic Solution of the Invention | |
|---|---|
| Ketorolac Tromethamine | 0.4% |
| CMC, Med Visc. | 0.65% |
| CMC Low Visc. | 0.35% |
| Potassium chloride | 0.14% |
| Calcium chloride, dihydrate | 0.060% |
| Magnesium chloride, hexahydrate | 0.060% |
| Boric acid | .060% |
| Sodium borate | .1225% |

Example 2

Unless otherwise specified, all steps in this procedure were carried out at room temperature. The following procedure was followed in accordance with the amounts listed in Table 2 below. Purified water at 90% of batch size was charged into the main batch vessel. Mixing was initiated to produce a vortex sufficient to disperse and/or dissolve all product ingredients without excessive aeration or foam formation. The following components were added directly into the vortex in order, allowing each to dissolve before adding the next: sodium chloride, edetate disodium, octoxynol-40 (as a 70% stock solution) and benzalkonium chloride (as a 10% stock solution). The amount of benzalkonium chloride added took into account the assay of the stock solution used. The solution was mixed for no longer than 15 minutes. A specified amount of 1N sodium hydroxide, 1.85 mL per liter of final bulk product, was then added. The pH was checked and if needed was adjusted to 10.7-11.0 with 1N sodium hydroxide or 1N hydrochloric acid. Ketorolac tromethamine was then added based on "as is" assay and mixed until completely dissolved based on visual inspection. When dissolved, the solution pH was again checked and if needed adjusted to pH 7.3-7.5 (final target pH is 7.4) with 1N sodium hydroxide or 1N hydrochloric acid. Purified water was then added to bring the bulk solution to final volume and allowed to mix for at least 15 minutes to ensure uniformity. The solution was then sterile filtered for use.

TABLE 2

0.4% Ketorolac Tromethamine Ophthalmic Solution (Comparative)

| | |
|---|---|
| Ketorolac Tromethamine | 0.4% |
| Edetate Disodium | 0.015% |
| NaCl | 0.79% |
| Benzalkonium Chloride | 0.006% |
| Octoxynol-40 | 0.003% |
| Ph | 7.4 |

Example 3

This example was prepared according to the procedure of Example 1, except that hydroxypropyl cellulose was used in place of the sodium carboxymethyl cellulose in an amount sufficient to provide a viscosity equivalent to the viscosity of the composition of Example 1.

Example 4

The following composition was manufactured on a volume basis at ambient temperates from two principal parts. Each part is manufactured separately and then combined under controlled sequences to form a sterile bulk product: the first part (Part 1) involves the dissolution of carboxymethyl cellulose sodium in water followed by bulk heat sterilization, and the second part (Part 2) involves dissolution of ketorolac tromethamine and salts in water sterile filtration throng a 0.2 micron membrane into a sterile pressure vessel. The sterile bulk solution is then clarity filtered through a 20 micron polypropylene membrane filter into the filling machine reservoir.

The sterile post-clarity filtered solution is then filled by a UD filling machine via blow-fill-seal process into UD vials using virgin LDPE resin without colorant. The filling is done in an ISO Class 5 environment. The nominal fill is 0.4 mL into 0.9 mL capacity vials.

TABLE 3

0.45% w/v Ketorolac Tromethamine Ophthalmic Solution

| Ingredient | Function | Concentration (% w/v) |
|---|---|---|
| Ketorolac tromethamine | Active | 0.45% |
| Carboxymethy cellulose Sodium (Med. Viscosity) | Thickening Agent | 0.325% |
| Carboxymethy cellulose Sodium (High Viscosity) | Thickening Agent | 0.175% |
| NaCl | Tonicity Agent | 0.7% |
| Sodium Citrate Dihydrate | Buffer | 0.2% |
| Sodium Hydroxide (1N) | pH adjustment | Adjust to pH 6.8 |
| Hydrochloric Acid (1N) | pH adjustment | Adjust to pH 6.8 |
| Purified Water | Vehicle | Q.S. |

Example 5

Comparison of Aqueous Humor Ketorolac Pharmacokinetics Following a Single Ocular Instillation of 0.45% Ketorolac Tromethamine Formulations with Varying pH to Acular LS® in New Zealand White Rabbits.

Study Objectives:
1) To compare aqueous humor ketorolac pharmacokinetics following a single ocular instillation of 0.45% ketorolac tromethamine formulations with varying pH and Acular LS® to New Zealand White rabbits;
2) This Example was designed to determine whether decreasing the pH of the composition would increase the absorption of ketorolac into the eye; and,
3) In addition, one arm of this trial was designed to test the effect of decreasing viscosity of the composition from 22 cps to 11 cps.

The specifics of this study are as follows:
Rabbit Aqueous Humor Ketorolac Concentrations following Administration of Three 0.45% Ketorolac Tromethamine Formulations and Acular LS

TABLE 4

| | |
|---|---|
| Treatment Groups | 0.45% Ketorolac Tromethamine 22 cps pH = 7.4 |
| | 0.45% Ketorolac Tromethamine 22 cps pH = 7.2 |
| | 0.45% Ketorolac Tromethamine 22 cps pH = 7.0 |
| | 0.45% Ketorolac Tromethamine 11 cps pH = 7.0 |
| | 0.45% Ketorolac Tromethamine 22 cps pH = 6.8 |
| | Acular LS pH = 7.4 |
| Dosing Route: | Topical ocular |
| Animal Gender: | NZW Rabbits/Female |
| Dosing Regimen | Single dose, bilateral |
| Timepoints: | 1, 2 and 4 hrs post-dose |
| # Rabbits: | 3 rabbits/timepoint + 1 rabbit blank |
| | Total = 39 rabbits |
| Tissues/Matrices: | Aqueous Humor |
| Bioanalysis: | LC-MS/MS |
| Data analysis: | $AUC_{0-t}, C_{max}$ |

The results of the study are reported in Table 5, below.

TABLE 5

PK Parameters

| Formulation | $AUC_{0-4} \pm SE$ (ng · h/ml) | $C_{max} \pm SD$ (ng/ml) | Relative % F* |
|---|---|---|---|
| 0.45% CMC 22 cps pH 7.4 w.o "outlier" | 627 ± 51 | 265 ± 71 | 135 |
| 0.45% CMC 22 cps pH 7.4 | 713 ± 96 | 322 ± 153 | 153 |
| 0.45% CMC 22 cps pH 7.2 | 620 ± 50 | 240 ± 84 | 133 |
| 0.45% CMC 22 cps pH 7.0 | 658 ± 73 | 268 ± 125 | 142 |
| 0.45% CMC 22 cps pH 6.8 | 939 ± 163 | 389 ± 258 | 202 |
| 0.45% CMC 11 cps pH 7.0 | 649 ± 74 | 347 ± 218 | 139 |
| Acular LS ® | 465 ± 65 | 211 ± 106 | 100 |

Summary of the Results

The sodium carboxymethyl cellulose-containing formulations perform better than Acular LS® with a relative bioavailability ranging from 133% (0.45% Keto 22 cps pH 7.2) to 202% (0.45% Keto 22 cps pH 6.8). However, there is not a clear pH effect—because the 0.45% Keto 22 cps pH 7.4 has a relative bioavailability of 153%, although one anomalous result maybe driving this observation. Nevertheless, the solution having a pH of 6.8 shows the best bioavailability.

Example 6

A multicenter, randomized, double-masked, parallel-group study is carried out using the 0.4% ketorolac tromethamine formulations of Examples 2 and 3. The study subjects consisted of 157 patients (78-79/group) undergoing unilateral PRK surgery. The key inclusion criteria for the study is that each subject a) is a candidate for unilateral photorefractive keratectomy surgery (PRK) within 7 days after the initial visit, b) have best-corrected ETDRS visual acuity of 20/100 or better, and c) is capable of wearing a soft bandage contact lens. Key exclusion criteria are a history of refractive ocular surgery and sensitivity to study medication or its vehicle, Tylenol #3®, or Ocuflox®. The patient demographics are shown in Table 6. A total of 157 patients are enrolled with an age range of 20-66 years. There are no significant demographic differences between treatment groups.

TABLE 6

Patient Demographics

|  | n | % |
|---|---|---|
| Gender |  |  |
| Female | 91 | 58 |
| Male | 66 | 42 |
| Age, mean ± SD | 39 ± 10 |  |
| Race |  |  |
| Caucasian | 148 | 94 |
| Black | 5 | 3 |
| Hispanic | 2 | 1 |
| Asian | 1 | 1 |
| Other | 1 | 1 |

Each subject receives the Ocuflox® 5 min prior to study medication. The study subjects then receive ketorolac tromethamine 0.4% ophthalmic solution of Example 2 or Example 3, 1 drop QID for up to 4 days. Then all subjects are then instructed to take Tylenol #3® as needed for intolerable pain (escape medication). Patients use electronic diaries with date and time stamp to record the ocular pain they experience as one of the following: no pain; mild; moderate; severe; and intolerable.

The pain intensity is less for the subjects who receive the solution of Example 2 during the first 12 hours post-PRK compared to those who receive the solution of Example 3. In particular, during the first 12 hours post-PRK, the group that receive the solution of Example 2 had fewer patients with severe or intolerable pain compared with the receive the solution of Example 3. In particular, the median pain intensity reported by the group which receive the solution of Example 2 was 1 grade less than with the group which receive the solution of Example 3 (moderate vs. severe on a 5-point scale of 0=no pain to 4=intolerable pain). Additionally, pain intensity is also less for the group which receive compared with the group which receive the solution of Example 3.

This clinical study shows that the solution of invention provides a greater degree of absorption of ketorolac as compared to the solution without sodium carboxymethyl cellulose despite the fact that the solutions have the same concentration of ketorolac and are at the same viscosity.

In summary, the 0.4% ketorolac formulation is clinically effective in treating post PRK ocular pain. In patients treated with 0.4 ketorolac tromethamine—the patients treated with the solution comprising sodium carboxymethyl cellulose experienced significantly greater and faster pain relief, and used less escape medication compared to the patients treated with the solution comprising hydroxypropylcellulose.

Example 7

Rabbit Ocular Pharmacokinetic Evaluation of Ketorolac Tromethamine 0.45%

Figures 3, 4:
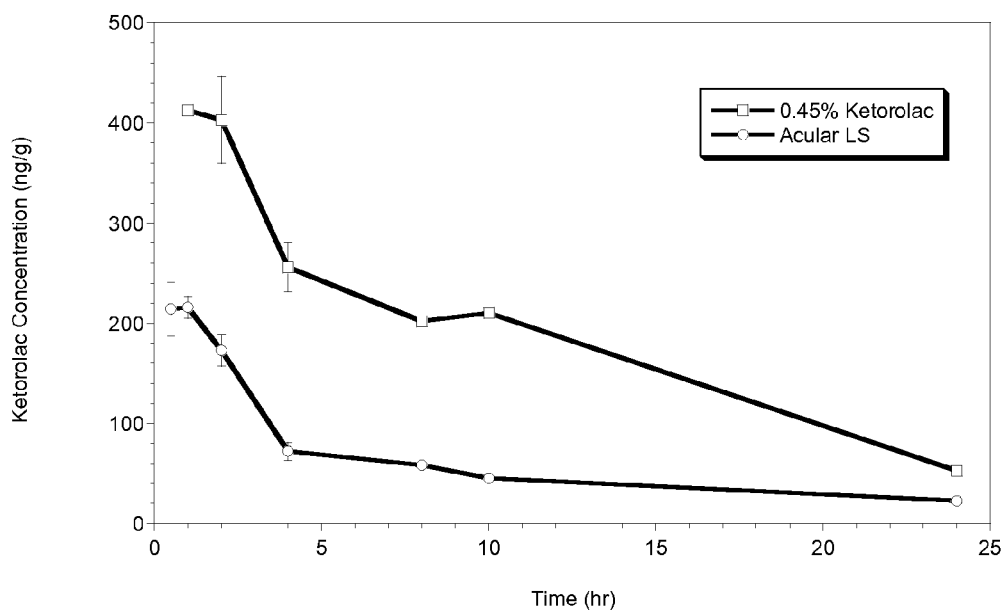
FIG. 3 shows the ocular pharmacokinetics of the results in Example 7 of the increased and prolonged ketorolac exposure in the iris-ciliary body of 0.45% w/v ketorolac solution in comparison to ACULAR LS®.
FIG. 4 shows the results of FIG. 3 in table form of Cmax, AUC and percent relative bioavailability of the increased and prolonged exposure in the iris ciliary body of 0.45% w/v ketorolac solution in comparison to ACULAR LS®.
Figure 5:
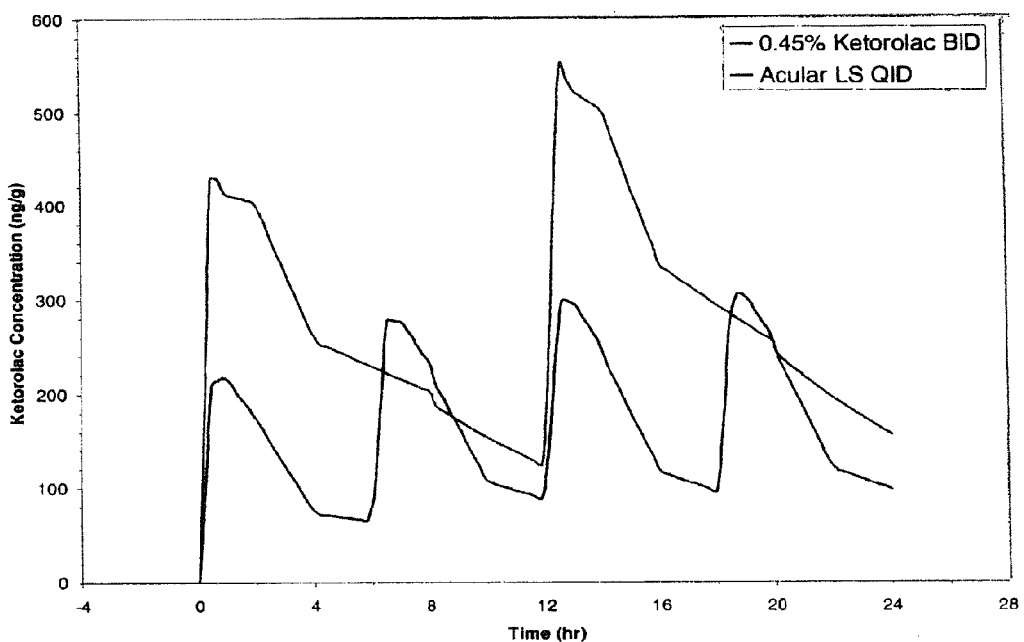
FIG. 5 shows a multiple dose simulation of Example 7 of 0.45% ketorolac BID in comparison to ACULAR LS® QID in the iris ciliary body; and, FIG. 6 shows safety and tolerability results in human clinical trials of 0.45% w/v ketorolac solution vs. ACULAR LS.

NZW Rabbits/Female
Dosing Regimen: Single ocular dose, bilateral
Timepoints: 0.5, 1, 2, 4, 8, 10 and 24 hrs post-dose
Tissues/Matrices: Aqueous Humor and Iris-ciliary body
Bioanalysis: LC-MS/MS
Data Analysis: Pharmacokinetic analyses and simulation Conclusion As shown in FIGS. 1-5, Example 7 shows there is an:
1) Increase in relative bioavailability of ketorolac as compared to Acular LS®;
2) Increased ketorolac concentrations are maintained longer post-dose; and
3) Together these data support a reduction in dosing frequency from 4×/day to 2×/day.

As shown in FIG. 6, Acular 0.45% is safe and well-tolerated among human patients when given 5 times over a half-day and compares very favorably to ACULAR LS.

Visual Acuity in Operative Eye

This summary of clinical safety (SCS) is based on 2 completed phase 3 studies of identical design and on one completed phase 1 study. All 3 studies support the safe use of a new formulation of ketorolac tromethamine ophthalmic solution 0.45% w/v (henceforth referred to as ketorolac 0.45%), an unpreserved formulation of ketorolac tromethamine ophthalmic solution containing a mixture of medium and high-molecular carboxymethyl cellulose (CMC). The formulation was used in the phase 3 studies, which investigated the safety of ketorolac 0.45% in cataract surgery patients. The phase 1 study investigated the safety of ketorolac 0.45% in healthy adult volunteers.

The current labeling for approved formulations of ketorolac tromethamine ophthalmic solution such as ACULAR LS® (0.40% w/v ketorolac) lists from 20% to 40% transient stinging and burning on instillation. The 0.45% formulation used in the phase 3 studies that form the basis of this application was developed, among other reasons, to improve comfort when administered in the eye, primarily by the addition of medium and high molecular weight carboxymethyl cellulose and the removal of octoxynol and benzalkonium chloride (BAK).

Studies evaluated efficacy and safety of ketorolac 0.45% compared with vehicle (same composition without the active) for the treatment of anterior chamber inflammation, ocular pain, and inhibition of surgically induced miosis following cataract extraction with posterior chamber intraocular lens (IOL) implantation. Both studies demonstrated that ketorolac 0.45% was safe and well tolerated. No new or unexpected safety findings were observed in either study. In addition, ketorolac 0.45% was found to be very well tolerated with a very low incidence of burning and stinging.

Another study assessed the safety and tolerability of ketorolac tromethamine ophthalmic solutions 0.35% and 0.45% compared with ACULAR LS® 0.4% in healthy adult subjects. ACULAR LS® 0.4% was chosen for comparison as it was known to be a better tolerated formulation than original ACULAR® (0.50% w/v ketorolac) due to the lower concentration of ketorolac and removal of BAK and octoxynol. Compared with ACULAR LS® 0.4%, ketorolac 0.45% had a consistently lower incidence of ocular symptoms such as burning/stinging and ocular discomfort when dosed 5 times in 1 day. No new or unexpected safety findings were observed for any of the ketorolac formulations.

The ketorolac 0.45% formulation of the present invention was characterized in ocular and systemic ketorolac rabbit pharmacokinetic and toxicokinetic studies, in addition to 1-day ocular tolerability, 1-month ocular toxicity, and 6-day ocular wound healing studies. From the results of these pre-clinical studies, 0.45% ketorolac tromethamine administered twice per day was anticipated to deliver ketorolac to ocular tissues that are efficacious but at lower levels than those previously demonstrated to be safe in long term toxicology studies.

The phase 3 studies were of identical design, multi-center, randomized, double-masked, parallel group comparison studies conducted to assess the safety and efficacy of ketorolac 0.45% compared with vehicle. Study patients underwent cataract extraction surgery with posterior chamber IOL implantation. Ketorolac 0.45% or vehicle was self-administered by patients (1 drop twice daily in the operative eye beginning on the day before surgery and continuing on the day of surgery through the first 2 weeks following surgery) and administered by medical personnel (3 drops during the 2 hr prior to surgery and 1 drop after surgery). The safety parameters assessed were adverse events, vital signs, intraocular pressure, visual acuity, biomicroscopy, and opthalmoscopic examinations. The studies consisted of 7 scheduled visits: screening (week −4 to day −2); randomization (day −3 to day −1); cataract surgery day; and postoperative days 1, 3, 7, and 14. Patients receiving ketorolac 0.45% had a lower incidence of ocular adverse events and of adverse events that led to discontinuation than patients receiving vehicle.

A phase 1 study, a single-center, randomized, double-masked, paired-eye, active-controlled study in healthy adult subjects assessing the safety and tolerability of ketorolac tromethamine ophthalmic solutions 0.35% and 0.45% compared with ACULAR LS® 0.4% (5 doses administered on 1 day). Five times in one day, administered by site personnel, subjects received 1 drop of ketorolac 0.45% in study eye/ACULAR LS® in fellow eye or 1 drop of ketorolac 0.35% in study eye/ACULAR LS® in fellow eye. The safety parameters assessed were ocular symptoms, ocular comfort, adverse events, vital signs, intraocular pressure, visual acuity, biomicroscopy, macroscopic bulbar hyperemia, and opthalmoscopic exam. The study consisted of 2 scheduled visits: screening (day −14 to day −1) and dosing day/exit (day 1). Ketorolac 0.45% had a consistently lower incidence of ocular symptoms and signs compared with ACULAR LS® 0.4%.

TABLE 7

Description of Clinical Efficacy and Safety Studies

| Number of Study Centers Locations | Start date End date Enrollment | Design Control type | Active/control, Route & Regimen | Study Objective | Subjects entered[a]/ completed | Duration | Gender M/F Median Age (Range) | Diagnosis and Inclusion Criteria | Safety Endpoints |
|---|---|---|---|---|---|---|---|---|---|
| 26 United States | 15 Oct. 2007 15 Apr. 2008 | Randomized, double-masked, parallel, vehicle-controlled | ketorolac 0.45% ophthalmic BID vehicle BID | Efficacy and safety | 248/201 | 16 days | 107/141 70 (40-89) | Planned cataract extraction with posterior chamber IOL implant | Adverse events, vital signs, intraocular pressure, visual acuity, biomicroscopy, fundus examinations |
| 22 United States | 19 Oct. 2007 31 Mar. 2008 | Randomized, double-masked, parallel, vehicle-controlled | ketorolac 0.45% ophthalmic BID vehicle BID | Efficacy and safety | 263/222 | 16 days | 111/152 69 (28-94) | Planned cataract extraction with posterior chamber IOL implant | Adverse events, vital signs, intraocular pressure, visual acuity, biomicroscopy, fundus examinations |

Abbreviations: IOL = intraocular lens
[a]Intent to treat (ITT) population

TABLE 8

Description of Clinical Safety Study

| Number of Study Centers Locations | Start date End date Enrollment | Design Control type | Active/control, Route & Regimen | Study Objective | Subjects entered/ completed | Duration | Gender M/F Median Age (Range) | Diagnosis and Inclusion Criteria | Safety Endpoints |
|---|---|---|---|---|---|---|---|---|---|
| 1 United States | 03 Jul. 2007 03 Jul. 2007 | Randomized, double-masked, paired-eye, active-control | Ketorolac 0.35%, 0.45%, 5 drops ophthalmic ACULAR LS ® 0.4%, 5 drops | Safety | 39/39 | 1 day | 14/25 24 (19-63) | Healthy adult volunteers | Adverse events, ocular symptoms, subject comfort questionnaires, vital signs, intraocular pressure, visual acuity, |

TABLE 8-continued

Description of Clinical Safety Study

| Number of Study Centers Locations | Start date End date Enrollment | Design Control type | Active/control, Route & Regimen | Study Objective | Subjects entered/ completed | Duration | Gender M/F Median Age (Range) | Diagnosis and Inclusion Criteria | Safety Endpoints |
|---|---|---|---|---|---|---|---|---|---|
| | | | | | | | | | macroscopic bulbar hyperemia, and biomicroscopy |

In a two phase 3 studies pooled, more than ⅔ of patients in both treatment groups experienced at least 1 line of improvement in visual acuity from baseline to final evaluation. Two patients in each treatment group had a decrease in visual acuity of >3 lines (0.6% [2/320] of ketorolac 0.45% patients, 1.3% [2/158] of vehicle patients).

The proportion of ketorolac 0.45%-treated patients who experienced at least 3 lines of improvement was statistically significantly higher than the proportion of vehicle-treated patients (58.1% [186/320] of ketorolac 0.45% patients, 41.1% [65/158] of vehicle patients, p<0.001). Statistical significance for the same comparison was observed in study −006 (p=0.002) but borderline significant in study −005 (p=0.054).

TABLE 9

Visual Acuity in Operative Eye: Final Evaluation Compared with Baseline (Safety Population)

| | Study | | Study | | Pooled | |
|---|---|---|---|---|---|---|
| Change (lines)[a] | Ketorolac 0.45% (N = 157) | Vehicle (N = 81) | Ketorolac 0.45% (N = 173) | Vehicle (N = 82) | Ketorolac 0.45% (N = 330) | Vehicle (N = 163) |
| N | 153 | 78 | 167 | 80 | 320 | 158 |
| ≥+3 | 91 (59.5) | 36 (46.2) | 95 (56.9) | 29 (36.3) | 186 (58.1) | 65 (41.1) |
| <+3 | 62 (40.5) | 42 (53.8) | 72 (43.1) | 51 (63.8) | 134 (41.9) | 93 (58.9) |
| ≥+2 to <+3 | 17 (11.1) | 12 (15.4) | 21 (12.6) | 7 (8.8) | 38 (11.9) | 19 (12.0) |
| ≥+1 to <+2 | 28 (18.3) | 12 (15.4) | 31 (18.6) | 19 (23.8) | 59 (18.4) | 31 (19.6) |
| ≥0 to <+1 | 12 (7.8) | 7 (9.0) | 10 (6.0) | 13 (16.3) | 22 (6.9) | 20 (12.7) |
| ≥−1 to <0 | 4 (2.6) | 4 (5.1) | 5 (3.0) | 6 (7.5) | 9 (2.8) | 10 (6.3) |
| ≥−2 to <−1 | 1 (0.7) | 5 (6.4) | 3 (1.8) | 6 (7.5) | 4 (1.3) | 11 (7.0) |
| >−3 to <−2 | 0 (0.0) | 0 (0.0) | 0 (0.0) | 0 (0.0) | 0 (0.0) | 0 (0.0) |
| ≤−3 | 0 (0.0) | 2 (2.6) | 2 (1.2) | 0 (0.0) | 2 (0.6) | 2 (1.3) |

[a]positive change represents improvement

In the phase 1 study, most subjects had no change in visual acuity during treatment. Decreases in visual acuity during treatment with respect to baseline were observed for 1 (5.0%) ketorolac 0.45%-treated eye, 1 (5.3%) ketorolac 0.35%-treated eye, and 3 (7.7%) ACULAR LS®-treated eyes.

Conclusions:
1) The impact of treatment on visual acuity favors ketorolac over vehicle;
2) More than ⅔ of patients in both treatment groups experienced at least 1 line of improvement in visual acuity from baseline to final evaluation;
3) Twice the percentage of patients in the vehicle group experienced a decrease in visual acuity of >3 lines; and,
4) The ketorolac 0.45% w/v group experienced over 40% greater incidence of patients experiencing at least 3 lines of improvement—a statistically significant difference.

The present invention is not to be limited in scope by the exemplified embodiments, which are only intended as illustrations of specific aspects of the invention. Various modifications, in addition to those disclosed herein, will be apparent to those skilled in the art by a careful reading of the specification, including the claims, as originally filed. It is intended that all such modifications will fall within the scope of the appended claims.

What is claimed is:

1. A topical aqueous ophthalmic solution for use in treating pain or inflammation, wherein said solution comprises 0.45% w/v ketorolac and about 0.5% w/v carboxymethyl cellulose, with no preservative and having a pH within the range of approximately 6.8-7.4.

2. The topical aqueous ophthalmic solution of claim 1, wherein the ketorolac is ketorolac tromethamine and is present in a concentration of 0.45% w/v.

3. The topical aqueous ophthalmic solution of claim 1, wherein the carboxymethyl cellulose is a combination of medium and high viscosity sodium carboxymethyl cellulose.

4. The topical aqueous ophthalmic solution of claim 1, wherein the carboxymethyl cellulose is present in a concentration of 0.5% w/v.

5. The topical aqueous ophthalmic solution of claim 4, having a pH of 6.8.

6. The topical aqueous solution of claim 1, wherein the solution is surfactant and chelator free.

7. The topical aqueous solution of claim 1, which is useful for treatment of ocular pain associated with postoperative photorefractive keratectomy.

8. The topical aqueous solution of claim 1, wherein the ophthalmic solution improves the visual acuity in a patient of at least one line of improvement.

9. The topical aqueous solution of claim 1, further comprising a mixture of medium and high viscosity sodium carboxymethyl cellulose, sodium chloride, sodium citrate dihydrate, sodium hydroxide, hydrochloric acid and purified water and wherein the solution improves the visual acuity of a user.

10. The topical aqueous solution of claim 1, wherein the combination of carboxymethyl cellulose and ketorolac increases the absorption in the eye of a patient more than a solution of ketorolac alone.

11. The topical aqueous solution of claim 1, wherein the ketorolac tromethamine is present as a racemic mixture of R-(+) and S-(−)-ketorolac tromethamine.

12. The topical aqueous solution of claim 1, wherein the viscosity is from 10 to 30 cps.

13. The topical aqueous solution of claim 1, wherein the solution may be administered before or after eye surgery to prevent ocular pain.

14. The topical aqueous solution of claim 1, wherein the solution increases healing time of the eye after surgery in comparison to ketorolac solutions containing a preservative.

15. The topical aqueous solution of claim 1, wherein the topical aqueous solution is instilled twice daily to achieve proper efficacy.

16. The topical aqueous solution of claim 1, wherein the ophthalmic improves visual acuity in a user of at least three lines of improvement.

17. A topical aqueous ophthalmic solution for use in treating pain or inflammation, wherein said solution comprises 0.45% w/v ketorolac tromethamine, about 0.5% w/v carboxymethyl cellulose, about 0.7% w/v NaCl and about 0.2% sodium citrate dehydrate and having a pH of about 6.8.

18. The topical aqueous ophthalmic solution of claim 17 wherein the solution is at a pH of 6.8.

19. The topical aqueous ophthalmic solution of claim 17, wherein said solution comprises 0.45% w/v ketorolac tromethamine, 0.5% w/v carboxymethyl cellulose, about 0.7% w/v NaCl and about 0.2% sodium citrate dehydrate and having a pH of about 6.8.

20. The topical aqueous ophthalmic solution of claim 17, further comprising sodium hydroxide and hydrochloric acid to adjust the pH.

21. The topical aqueous ophthalmic solution of claim 17 for use in treating pain or inflammation after surgery.

22. The topical aqueous ophthalmic solution of claim 17 wherein the solution is applied at least once a day.

23. The topical aqueous ophthalmic solution of claim 17 wherein the solution is applied at least twice a day.

24. The topical aqueous ophthalmic solution of claim 17 wherein the solution is applied at least once a day starting one day prior to surgery.

25. The topical aqueous ophthalmic solution of claim 17 wherein the carboxymethyl cellulose is a mixture of medium and high viscosity carboxymethyl cellulose.

26. A topical aqueous ophthalmic solution of claim 17, wherein said solution comprises 0.45% w/v ketorolac tromethamine, 0.5% w/v carboxymethyl cellulose, 0.7% w/v NaCl, 0.2% sodium citrate dehydrate, water and having a pH of about 6.8.

* * * * *

UNITED STATES PATENT AND TRADEMARK OFFICE
CERTIFICATE OF CORRECTION

| | |
|---|---|
| PATENT NO. | : 9,192,571 B2 |
| APPLICATION NO. | : 12/552057 |
| DATED | : November 24, 2015 |
| INVENTOR(S) | : Eldon Q. Farnes et al. |

Page 1 of 2

It is certified that error appears in the above-identified patent and that said Letters Patent is hereby corrected as shown below:

On the Title page, in item (57), in column 2, in "Abstract", line 4, after "acuity" insert -- in users --.

In item (57), in column 2, in "Abstract", line 6, delete "that" and insert -- which --, therefor.

On page 2, in item (56), in column 1, under "Other Publications", line 9, delete "Institues" and insert -- Institutes --, therefor.

On page 2, in item (56), in column 2, under "Other Publications", line 16, delete "Dlclofenac" and insert -- Diclofenac --, therefor.

On page 2, in item (56), in column 2, under "Other Publications", line 53, delete "Dislofenac" and insert -- Diclofenac --, therefor.

On page 3, in item (56), in column 1, under "Other Publications", line 44, delete "Salicyclic" and insert -- Salicylic --, therefor.

On page 3, in item (56), in column 1, under "Other Publications", line 48, delete "Myristy" and insert -- Myristyl --, therefor.

On page 3, in item (56), in column 2, under "Other Publications", line 31, delete "Keratechtomy," and insert -- Keratectomy, --, therefor.

On page 3, in item (56), in column 2, under "Other Publications", line 44, delete "Opthalmology," and insert -- Ophthalmology, --, therefor.

On page 3, in item (56), in column 2, under "Other Publications", line 62, delete "Ophthamol." and insert -- Ophthalmol. --, therefor.

On page 3, in item (56), in column 2, under "Other Publications", line 67, delete "Refreash TEARSn" and insert -- Refresh TEARS --, therefor.

In The Specification

In column 1, line 21, delete "benzyl" and insert -- benzoyl --, therefor.

In column 1, line 33, delete "Opthalmology," and insert -- Ophthalmology, --, therefor.

Signed and Sealed this
Eighth Day of March, 2016

Michelle K. Lee
*Director of the United States Patent and Trademark Office*

CERTIFICATE OF CORRECTION (continued)
U.S. Pat. No. 9,192,571 B2

In The Specification

In column 6, line 10, delete "a an" and insert -- a --, therefor.

In column 7, line 9 (TABLE 2), delete "Ph" and insert -- pH --, therefor.

In column 7, line 47 (TABLE 3), delete "Carboxymethy" and insert -- Carboxymethyl --, therefor.

In column 7, line 49 (TABLE 3), delete "Carboxymethy" and insert -- Carboxymethyl --, therefor.

In column 8, line 10, delete "LS" and insert -- LS. --, therefor.

In column 10, line 53, delete "(TOL)" and insert -- (IOL) --, therefor.

In column 12, line 2, delete "opthalmoscopic" and insert -- ophthalmoscopic --, therefor.

In column 12, lines 20-21, delete "opthalmoscopic" and insert -- ophthalmoscopic --, therefor.

In The Claims

In column 15, line 23, in claim 16, after "ophthalmic" insert -- solution --.